(12) United States Patent
Aattela

(10) Patent No.: US 10,502,722 B2
(45) Date of Patent: Dec. 10, 2019

(54) METHOD FOR INDOOR AIR ANALYSIS, AND SAMPLING ARRANGEMENT

(71) Applicant: SISÄILMATUTKIMUSPALVELUT ELISA AATTELA OY, Tampere (FI)

(72) Inventor: Elisa Aattela, Tampere (FI)

(73) Assignee: SISÄILMATUTKIMUSPALVELUT ELISA AATTELA OY, Tampere (FI)

( * ) Notice: Subject to any disclaimer, the term of this patent is extended or adjusted under 35 U.S.C. 154(b) by 263 days.

(21) Appl. No.: 15/502,939

(22) PCT Filed: Dec. 23, 2015

(86) PCT No.: PCT/FI2015/050942
§ 371 (c)(1),
(2) Date: Feb. 9, 2017

(87) PCT Pub. No.: WO2016/107980
PCT Pub. Date: Jul. 7, 2016

(65) Prior Publication Data
US 2018/0209948 A1    Jul. 26, 2018

(30) Foreign Application Priority Data
Dec. 30, 2014 (FI) .................... 20146159

(51) Int. Cl.
*G01N 33/00* (2006.01)
*G01N 1/42* (2006.01)
*G01N 1/22* (2006.01)

(52) U.S. Cl.
CPC .......... *G01N 33/0016* (2013.01); *G01N 1/42* (2013.01); *G01N 2001/2282* (2013.01)

(58) Field of Classification Search
CPC ....... G01N 33/0016; G01N 2001/2282; G01N 1/42
USPC .................................. 73/863.11–12
See application file for complete search history.

(56) References Cited

U.S. PATENT DOCUMENTS

| | | | | |
|---|---|---|---|---|
| 3,956,921 A * | 5/1976 | Himes | ................ | G01N 1/2258 73/863.12 |
| 4,530,250 A * | 7/1985 | Gay | ..................... | B01D 46/543 62/532 |
| 4,964,278 A * | 10/1990 | Wen | ..................... | B01D 5/0027 62/55.5 |
| 5,211,679 A * | 5/1993 | Meyer | ................ | G01N 1/2273 73/863.12 |
| 5,501,080 A | 3/1996 | McManus et al. | | |
| 7,392,689 B2 * | 7/2008 | Kim | ..................... | G01N 1/2273 73/31.02 |

(Continued)

FOREIGN PATENT DOCUMENTS

JP     2005-78362 A     3/2005
WO   WO 2014/147696 A1   3/2005

*Primary Examiner* — Nathaniel J Kolb
(74) *Attorney, Agent, or Firm* — Birch, Stewart, Kolasch & Birch, LLP

(57) ABSTRACT

A method for indoor air analysis, and a sampling arrangement are disclosed. The method includes taking a sample from indoor air in such a way that a surface is cooled to be so cold that water molecules of the indoor air undergo deposition on the surface, whereby frost is generated on the surface; defrosting the frost into water; and analysing the quality of the indoor air from the water.

13 Claims, 2 Drawing Sheets

(56) References Cited

U.S. PATENT DOCUMENTS

| | | | | |
|---|---|---|---|---|
| 8,201,465 B2* | 6/2012 | Baron | ............... | G01N 1/22 |
| | | | | 73/863.11 |
| 9,804,071 B2* | 10/2017 | Inoue | ............... | G01N 1/42 |
| 2007/0151326 A1* | 7/2007 | Kim | ............... | G01N 1/2273 |
| | | | | 73/31.02 |
| 2009/0255350 A1* | 10/2009 | Decker | ............ | G01N 1/4022 |
| | | | | 73/863.12 |
| 2009/0301228 A1* | 12/2009 | Baron | ............... | G01N 1/22 |
| | | | | 73/863.11 |
| 2009/0326338 A1* | 12/2009 | Kobayashi | ......... | A61B 5/083 |
| | | | | 600/300 |
| 2015/0355061 A1* | 12/2015 | Inoue | ............... | G01N 1/42 |
| | | | | 73/863.11 |

* cited by examiner

METHOD FOR INDOOR AIR ANALYSIS, AND SAMPLING ARRANGEMENT

BACKGROUND OF THE INVENTION

The invention relates to a method for indoor air analysis and to a sampling arrangement.

The quality of indoor air is generally analysed with the pre-supposition that solid particles in indoor air contain some harmful impurities. In sampling the aim is to collect solid particles from indoor air, the sample obtained being then analysed. Particles may be collected by, for example, filtering indoor air.

Further, a sample may be generated by collecting room dust settled on horizontal surfaces. A solution is also known where the sample is generated by condensing water vapour of indoor air into liquid in a collection receptacle. In this solution, the surface of the collection receptacle is cooled to 3° C. Thus, water vapour from indoor air condenses on the surface of the collection receptacle. If the indoor air humidity is sufficient, it takes a few days to collect a water amount sufficient to enable an analysis of the indoor air quality, based on the water collected from the air.

BRIEF DESCRIPTION OF THE INVENTION

An object of this invention is to provide a method of a novel type for analysing indoor air, and a sampling arrangement.

The solution according to the invention is characterized by what is disclosed in the independent claims. Some embodiments of the invention are presented in the dependent claims.

The solution disclosed comprises taking a sample from the indoor air in such a way that a surface is cooled to be so cold that the water molecules of the indoor air undergo deposition on the surface, whereby frost is generated on the surface. The generated frost is defrosted into water. An analysis of the water collected from the indoor air is performed, the indoor air quality being concluded from this analysis. Bound to water molecules, there may be impurities that may be in gas, liquid and/or gas state. Impurities include—as some examples—nanoparticles generated in incomplete combustion, and moulds' gaseous metabolic products. Impurities may be harmful in many ways. Analysing the water sample enables determination of the number of harmful substances in the indoor air. By means of the presented solution, the required amount of water can be collected very fast. Typically, for example, a few hours are enough to collect a sufficient amount of water.

The idea of an embodiment is that a surface is cooled such that cooling material, such as dry ice, is provided in connection with the surface. In this way, the surface can be cooled fast, efficiently and simply.

In accordance with an embodiment, the surface is the outer surface of a flat box, and the cooling material is provided inside the box. In this way, the area of the surface to be cooled can be made large and, all in all, the construction is simple and reliable.

The presented solution allows, for instance, the sampling to be repeated reliably. Further, a single space may be provided with several sampling collectors. Thus, the required number of samples can be collected fast, and/or a sufficient sample amount can be collected at a time for several analyses.

BRIEF DESCRIPTION OF THE FIGURES

The invention will now be described in greater detail in the context of preferred embodiments and with reference to the attached drawings, of which.

DETAILED DESCRIPTION OF THE INVENTION

Figure 1:
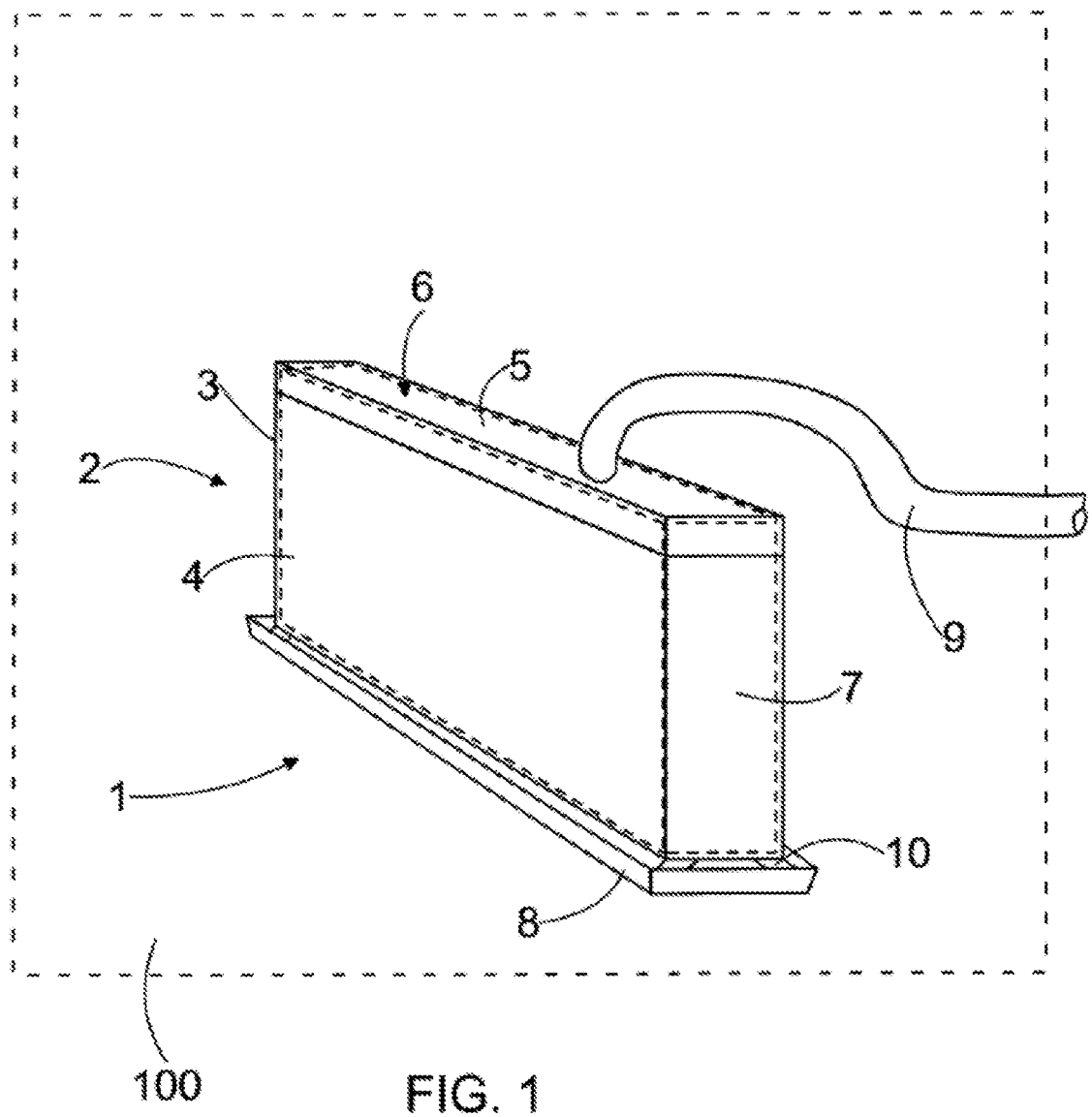
FIG. 1 shows a sampling arrangement and a method according to the invention.

FIG. 1 shows a sampling arrangement and method according to the invention.

A sampling arrangement 1 is arranged in an interior 100 which may be for example a room, such as a dwelling room, office room, public space or the like. The interior 100 contains indoor air.

The sampling arrangement 1 comprises a sampling collector 2 comprising a surface 3 to be cooled. In the present embodiment, the surface 3 to be cooled is designed to be a box 4 each surface of which is rectangular. However, it is clear that the shape of the surface 3 to be cooled may also be different.

The material of the surface 3 to be cooled may be for instance metal, such as steel, preferably stainless steel, or any material that withstands the temperature variations of the surface 3 and from which no substances harmful to the analysis of indoor air are released.

In accordance with an idea, the material is stainless steel with a thickness of 1 mm, the dimensions of the box being, for instance, 520×240×30 mm. However, it should be emphasized that said dimensions are merely examples and that different dimensions are also feasible in the implementation.

Nevertheless, the box 4 is preferably flat. Thus, the size of the surface 3 can be made large relative to the volume of the box 4. In this way, the box gathers frost most efficiently. In accordance with an embodiment, the box 4 is so flat that its area is at least 30% larger than the area of a cube having a corresponding volume.

The box 4 comprises an interior 6 to be accessed from outside through an openable lid 5. The interior 6 may be provided with cooling material 7 shown by broken lines in FIG. 1. The cooling material 7 is provided in connection with the surface 3 in such a way that it cools the surface 3.

In accordance with an idea, the cooling material 7 is dry ice, i.e. carbon dioxide ice, i.e. carbon dioxide in solid form. Dry ice allows the surface 3 to be cooled to a very low temperature because the temperature of dry ice is approximately −78° C. or lower.

The cooling material 7 may be formed of, for example, one or more cooling material elements dimensioned to fit into the interior 6, grains with which the interior 6 is filled appropriately, or the like. When provided in connection with the surface 3 in the interior 6, the cooling material 7 is solid.

The cooling material 7 cools the surface 3 so cold that water molecules of indoor air undergo deposition on the surface 3, as a result of which frost is generated on the surface out of these water molecules. The frost is mainly generated by deposition. The frost contains not only water molecules but also solids bound to them in various ways and contained in the room air.

The sampling collector 2 may further comprise a collection receptacle 8 for collecting the water melted out of frost. The collection receptacle 8 may also be a part separate from the sampling collector 2 and arranged underneath the sampling collector 2. The collection receptacle 8 is preferably detachable such that it and the water collected in it can be moved off the sampling collector 2, and the water can be, for example, poured into a sterile sample bottle.

In accordance with an idea, the box interior 6 is connected to the outside of the interior 100 through a channel 9. The channel 9 may be a hose, for instance. The channel 9 may be made of silicone, for instance. The first end of the channel 9 may be arranged for example on the lid 5 of the sampling collector 2. The second end of the channel 9 may be arranged for instance in the adjacent space or in connection with an exhaust air valve or directly in the outdoor air. In this way, it is possible to prevent the cooling material that is sublimating into gas, such as carbon dioxide generated out of dry ice, from getting into the interior 100.

In the lower part of the box 4, for example at its both ends, there may be legs 10. In such a case, frost can also be generated on the lower surface of the box 4, from where it can be collected in the collection receptacle 8.

Figure 2:
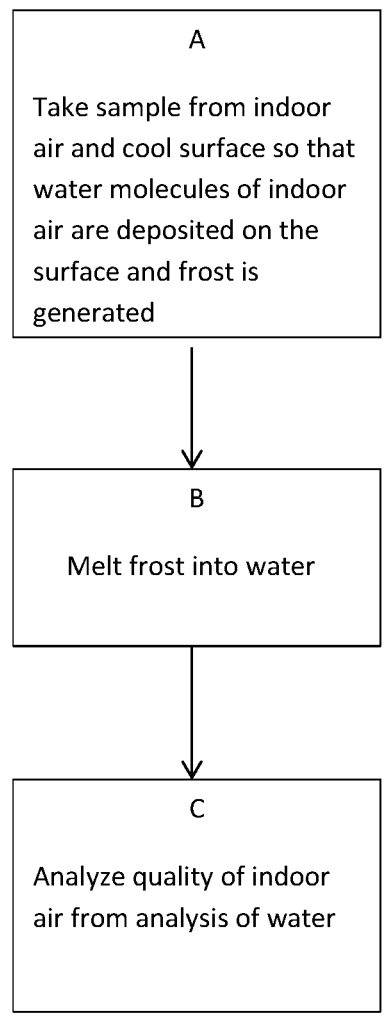
FIG. 2 shows method steps of a method according to the invention.

FIG. 2 shows method steps of a method according to the invention.

The method comprises taking a sample from the indoor air in such a way that in step A, a disinfected surface 3 is cooled to be so cold that water molecules of the indoor air undergo deposition on said surface. As a result, frost is generated on the surface.

The surface 3 to be cooled may be, for instance, the outer surface of the box 4.

The surface 3 may be cooled by cooling material, such as dry ice, provided in connection with the surface. The cooling material may be provided inside said box 4, for example.

In step B, the frost is defrosted into water. This may be implemented for instance by removing the cooling material 7 that cools the surface 3 from the connection of the surface, whereby the surface 3 begins to warm up due to the effect of the interior 100. Said removal may comprise for example removing cooling material elements or grains from the box interior 6. In accordance with an idea, warming of the surface may be accelerated by a heating element which may be, for example, a hot water bottle filled with warm tap water and arranged in the box interior 6.

In step B, the surfaces 3 and the collection receptacle 8 may further be treated by means of a suitable solvent, for instance 70% ethanol, and by recovering the used solvent and/or the towels used in the treatment or the like treatment means for later analysis.

In step C, the quality of the indoor air is analysed from the water. In particular, solids carried along with water into the sample may be analysed, both qualitatively and quantitatively.

Furthermore, step C may comprise analysing the used solvent recovered in step B and the treatment means, which allows the quality and quantity of fat-soluble substances possibly contained in the indoor air to be found out.

It is apparent to a person skilled in the art that as technology advances, the basic idea of the invention may be implemented in many different ways. The invention and its embodiments are thus not restricted to the examples described above but may vary within the scope of the claims.

The invention claimed is:

1. A method for sampling indoor air, the method comprising the steps of:
   providing a box having a plurality of sidewalls and an openable lid, the plurality of sidewalls and openable lid forming an interior of the box;
   adding a solid cooling material to the interior of the box through the openable lid;
   taking a sample from the indoor air in such a way that a surface an exterior surface of the box is cooled to be so cold that water molecules of the indoor air undergo deposition on the surface, whereby frost is generated on the surface;
   cooling the surface in such a way that the solid cooling material is provided in connection with the surface; and
   defrosting the frost into water.

2. The method according to claim 1, wherein the frost is defrosted into water in such a way that the cooling material is removed from the connection of the surface, and thus the surface is allowed to be warmed up.

3. The method according to claim 1, wherein the cooling material is dry ice.

4. The method according to claim 1, wherein the box is flat.

5. The method according to claim 1, further comprising accelerating warming of the surface by a heating element arranged inside the box.

6. The method according to claim 1, further comprising removing the solid cooling material from the box.

7. The method according to claim 1, further comprising adding a heating element to the box after removing the solid cooling material from the box.

8. The method according to claim 1, further comprising removing evaporating cooling material from the box with a hose attached to the box.

9. A sampling arrangement, comprising:
   a box having a plurality of sidewalls and an openable lid defining an interior; and
   a cooling arrangement for cooling an exterior surface in such a way that the exterior surface is cooled so cold that water molecules of the indoor air undergo deposition on the surface, whereby frost is generated on the surface, the cooling arrangement for cooling the surface comprising:
      solid cooling material to be provided in connection with the surface, the solid cooling material being removable from the interior of the box; and
      a collection receptacle for collecting water melted out of the frost.

10. The sampling arrangement according to claim 9, wherein the solid cooling material is dry ice.

11. The sampling arrangement according to claim 9, wherein in connection with the box, there is a hose for removing evaporating cooling material from the interior of the box.

12. The sampling arrangement according to claim 9, wherein the box is flat.

13. The sampling arrangement according to claim 9, further comprising a heating element for accelerating warming of the surface and arranged inside the box.

* * * * *